US011298276B2

(12) United States Patent
Barnhorst et al.

(10) Patent No.: US 11,298,276 B2
(45) Date of Patent: Apr. 12, 2022

(54) DIAPER ADAPTED FOR COLLECTION OF UNCONTAMINATED AND INTACT STOOL SAMPLE FROM AN INFANT

(71) Applicant: The Procter & Gamble Company, Cincinnati, OH (US)

(72) Inventors: Jacob Alan Barnhorst, Deerfield Township, OH (US); Masaharu Nishikawa, Cincinnati, OH (US); Jeromy Thomas Raycheck, South Lebanon, OH (US); Cornelia Beate Martynus, Nidderau-Ostheim (DE)

(73) Assignee: The Procter & Gamble Company, Cincinnati, OH (US)

(*) Notice: Subject to any disclaimer, the term of this patent is extended or adjusted under 35 U.S.C. 154(b) by 613 days.

(21) Appl. No.: 15/446,450

(22) Filed: Mar. 1, 2017

(65) Prior Publication Data

US 2017/0252233 A1 Sep. 7, 2017

Related U.S. Application Data

(60) Provisional application No. 62/301,679, filed on Mar. 1, 2016.

(51) Int. Cl.
*A61F 13/56* (2006.01)
*A61F 13/495* (2006.01)

(52) U.S. Cl.
CPC ........ *A61F 13/5638* (2013.01); *A61F 13/495* (2013.01); *A61F 2013/4953* (2013.01)

(58) Field of Classification Search
CPC combination set(s) only.
See application file for complete search history.

(56) References Cited

U.S. PATENT DOCUMENTS 2,610,629 A 9/1952 Hawkins
3,776,233 A 12/1973 Schaar
(Continued)

FOREIGN PATENT DOCUMENTS

CN 204274811 U 4/2015
EP 3072487 9/2016
(Continued)

OTHER PUBLICATIONS

Website: http://www.small-beginnings.com/#!blank/copk, Phototherapy Diapers 'Beary Small' Bili-Buns, 2015.
(Continued)

*Primary Examiner* — Guy K Townsend
(74) *Attorney, Agent, or Firm* — Daniel S. Albrecht; William E. Gallagher

(57) ABSTRACT

A diaper configured for collection of a stool sample for an infant, and an associated method for collection, are disclosed. The diaper may include a backsheet including an effectively urine- and feces-impermeable material; a transverse perineal barrier including an effectively urine- and feces-impermeable material and having a proximal portion overlying the backsheet and sealingly connected to the diaper, and a free distal edge; and a liquid control structure disposed over the backsheet. The diaper may include additional features configured to receive a discharge of urine, isolate fecal material from urine, and facilitate collection of an intact stool sample following elimination.

17 Claims, 8 Drawing Sheets

(56) References Cited

U.S. PATENT DOCUMENTS

| | | | |
|---|---|---|---|
| 4,231,370 A | 11/1980 | Mroz et al. | |
| 4,257,418 A | 3/1981 | Hessner | |
| 4,629,643 A | 12/1986 | Curro et al. | |
| 4,661,102 A | 4/1987 | Shikata | |
| 5,026,364 A | 6/1991 | Robertson | |
| 5,226,992 A | 7/1993 | Morman | |
| 5,342,338 A | 8/1994 | Roe | |
| 5,516,572 A | 5/1996 | Roe | |
| 5,714,156 A | 2/1998 | Schmidt et al. | |
| 5,827,259 A | 10/1998 | Laux et al. | |
| 5,906,604 A | 5/1999 | Ronnberg et al. | |
| 5,931,827 A | 8/1999 | Buell et al. | |
| 5,934,470 A | 8/1999 | Bauer | |
| 5,938,652 A | 8/1999 | Sauer | |
| 5,971,970 A | 10/1999 | Carlbark et al. | |
| 5,993,433 A | 11/1999 | St. Louis et al. | |
| 5,998,695 A * | 12/1999 | Roe | A61L 15/34 604/367 |
| 6,010,490 A | 1/2000 | Freeland et al. | |
| 6,010,491 A | 1/2000 | Roe et al. | |
| 6,018,093 A * | 1/2000 | Roe | A61L 15/18 604/367 |
| 6,075,178 A | 6/2000 | LaWilhelm et al. | |
| 6,120,486 A | 9/2000 | Toyoda et al. | |
| 6,132,410 A | 10/2000 | Van Gompel et al. | |
| 6,135,988 A | 10/2000 | Turner et al. | |
| 6,217,563 B1 | 4/2001 | Van Gompel et al. | |
| 6,315,764 B1 | 11/2001 | Faulks et al. | |
| 6,336,922 B1 | 1/2002 | VanGompel et al. | |
| 6,372,952 B1 * | 4/2002 | Lash | A61F 13/4946 604/369 |
| 6,395,955 B1 * | 5/2002 | Roe | G01N 33/5308 604/361 |
| 6,414,215 B1 | 7/2002 | Roe | |
| 6,471,716 B1 | 10/2002 | Pecukonis | |
| 6,491,677 B1 | 12/2002 | Glaug et al. | |
| 6,498,284 B1 | 12/2002 | Roe | |
| 6,551,295 B1 * | 4/2003 | Schmidt | A61F 13/5376 604/385.01 |
| 6,570,057 B1 * | 5/2003 | Schmidt | A61F 13/15203 604/378 |
| 6,603,403 B2 | 8/2003 | Jeutter et al. | |
| 6,627,786 B2 | 9/2003 | Roe et al. | |
| 6,638,262 B2 | 10/2003 | Suzuki et al. | |
| 6,659,993 B2 | 12/2003 | Minato et al. | |
| 6,664,439 B1 * | 12/2003 | Arndt | A61F 13/15203 604/368 |
| 6,680,422 B2 | 1/2004 | Roe | |
| 6,716,205 B2 | 4/2004 | Coenen et al. | |
| 6,720,471 B1 * | 4/2004 | Arndt | A61F 13/15203 604/367 |
| 6,767,344 B2 | 7/2004 | Suzuki | |
| 6,786,895 B1 | 9/2004 | Schmitz | |
| 6,790,203 B2 | 9/2004 | Een | |
| 6,817,993 B1 | 11/2004 | Simmons et al. | |
| 6,921,394 B2 | 7/2005 | Sayama et al. | |
| 6,989,187 B2 | 1/2006 | Thomas | |
| 7,033,340 B1 | 4/2006 | Muscat et al. | |
| 7,118,557 B2 | 10/2006 | Minato et al. | |
| 7,159,532 B2 | 1/2007 | Klofta et al. | |
| 7,163,530 B1 | 1/2007 | Toyoshima et al. | |
| 7,332,642 B2 | 2/2008 | Liu | |
| 7,419,562 B2 | 9/2008 | Van Gompel et al. | |
| 7,566,330 B2 | 7/2009 | Sugiyama et al. | |
| 7,666,173 B2 | 2/2010 | Mishima et al. | |
| 7,695,463 B2 | 4/2010 | LaVon et al. | |
| 7,744,576 B2 | 6/2010 | Busam et al. | |
| 7,753,899 B2 | 7/2010 | Mori et al. | |
| 7,772,455 B1 * | 8/2010 | Roe | A61F 13/51113 604/360 |
| 7,785,309 B2 | 8/2010 | Van Gompel et al. | |
| 7,794,441 B2 | 9/2010 | Ashton et al. | |
| 7,838,722 B2 | 11/2010 | Blessing et al. | |
| 7,838,723 B1 * | 11/2010 | Schmidt | A61F 13/15203 604/369 |
| 7,879,017 B1 | 2/2011 | Tabata et al. | |
| 8,017,827 B2 | 9/2011 | Hundorf et al. | |
| 8,043,272 B2 | 10/2011 | Long et al. | |
| 8,178,748 B2 | 5/2012 | Hammons et al. | |
| 8,180,603 B2 | 5/2012 | Blessing | |
| 8,181,278 B2 | 5/2012 | Odorzynski et al. | |
| 8,216,201 B2 | 7/2012 | Beck | |
| 8,231,592 B2 | 7/2012 | Suzuki et al. | |
| 8,274,393 B2 | 9/2012 | Ales et al. | |
| 8,430,858 B2 | 4/2013 | Bäck | |
| 8,449,518 B2 | 5/2013 | Allison-Rogers | |
| 8,496,637 B2 | 7/2013 | Hundorf et al. | |
| 8,502,012 B2 | 8/2013 | Meyer et al. | |
| 8,581,019 B2 | 11/2013 | Carlucci et al. | |
| 8,598,406 B2 | 12/2013 | Ponomarenko et al. | |
| 8,618,349 B2 | 12/2013 | Klofta | |
| 8,668,680 B2 | 3/2014 | Ichikawa et al. | |
| 8,679,391 B2 | 3/2014 | O'Donnell et al. | |
| 8,747,380 B2 | 6/2014 | Coates | |
| 8,764,721 B2 | 7/2014 | Van Gompel et al. | |
| 8,764,722 B2 | 7/2014 | Rhein et al. | |
| 8,894,626 B2 | 11/2014 | Beck | |
| 8,926,580 B2 | 1/2015 | Carney et al. | |
| 8,927,801 B2 | 1/2015 | Klofta | |
| 8,929,944 B2 | 1/2015 | Yam | |
| 8,933,292 B2 | 1/2015 | Abraham et al. | |
| 8,939,562 B2 | 1/2015 | Koike et al. | |
| 8,968,614 B2 | 3/2015 | Desai et al. | |
| 8,968,814 B2 | 3/2015 | Heino et al. | |
| 8,979,815 B2 | 3/2015 | Roe et al. | |
| 8,992,496 B2 | 3/2015 | Bäck | |
| 9,044,358 B2 | 6/2015 | Nakajima et al. | |
| 9,050,218 B2 | 6/2015 | Martynus et al. | |
| 9,050,219 B2 | 6/2015 | Martynus et al. | |
| 9,060,904 B2 | 6/2015 | Hundorf et al. | |
| 9,072,634 B2 | 7/2015 | Hundorf et al. | |
| 9,125,758 B2 | 9/2015 | Skreosen | |
| 9,168,181 B2 | 10/2015 | Popp et al. | |
| 9,216,116 B2 | 12/2015 | Roe et al. | |
| 9,241,839 B2 | 1/2016 | Abraham et al. | |
| 9,259,362 B2 | 2/2016 | Popp et al. | |
| 9,333,120 B2 | 5/2016 | Lavon et al. | |
| 9,445,951 B2 | 9/2016 | Moberg-alehammar et al. | |
| 9,464,369 B2 | 10/2016 | Isele et al. | |
| 9,486,368 B2 | 11/2016 | Nelson | |
| 9,554,948 B2 | 1/2017 | Song et al. | |
| 9,675,503 B2 | 6/2017 | Carney | |
| 9,713,557 B2 | 7/2017 | Arizti et al. | |
| 9,789,009 B2 | 10/2017 | Joseph | |
| 2001/0053902 A1 * | 12/2001 | Roe | A61L 15/18 604/385.01 |
| 2002/0035354 A1 * | 3/2002 | Mirle | B32B 5/22 604/385.01 |
| 2002/0091368 A1 * | 7/2002 | LaVon | A61F 13/505 604/385.14 |
| 2002/0111596 A1 | 8/2002 | Fletcher | |
| 2003/0050616 A1 | 3/2003 | Reynolds et al. | |
| 2003/0135176 A1 | 7/2003 | Delzer et al. | |
| 2003/0212376 A1 | 11/2003 | Walter | |
| 2004/0102757 A1 | 5/2004 | Olson | |
| 2004/0158213 A1 | 8/2004 | Ponomarenko et al. | |
| 2004/0230171 A1 | 11/2004 | Ando | |
| 2004/0254549 A1 | 12/2004 | Olson et al. | |
| 2005/0215962 A1 | 9/2005 | Litvay et al. | |
| 2006/0004340 A1 | 1/2006 | Ben-natan | |
| 2006/0048880 A1 | 3/2006 | Blessing et al. | |
| 2006/0247597 A1 | 11/2006 | Hogan et al. | |
| 2006/0264858 A1 | 11/2006 | Roe | |
| 2007/0049895 A1 | 3/2007 | Van Gompel | |
| 2007/0233027 A1 | 3/2007 | Roe et al. | |
| 2007/0088310 A1 | 4/2007 | Sugiyama et al. | |
| 2007/0093767 A1 | 4/2007 | Carlucci et al. | |
| 2007/0232180 A1 | 10/2007 | Polat | |
| 2008/0091159 A1 | 4/2008 | Carlucci et al. | |
| 2008/0269706 A1 | 10/2008 | Long et al. | |
| 2008/0269707 A1 | 10/2008 | Song | |
| 2008/0312619 A1 | 12/2008 | Ashton et al. | |

(56) References Cited

U.S. PATENT DOCUMENTS

| | | |
|---|---|---|
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312625 A1 | 12/2008 | Hundorf et al. |
| 2008/0312628 A1 | 12/2008 | Hundorf et al. |
| 2009/0138884 A1 | 5/2009 | Kakeda et al. |
| 2009/0318884 A1 | 12/2009 | Meyer et al. |
| 2010/0030173 A1 | 2/2010 | Song et al. |
| 2011/0015602 A1 | 1/2011 | Schmidt et al. |
| 2011/0137274 A1 | 6/2011 | Klofta et al. |
| 2011/0184372 A1 | 7/2011 | Esping et al. |
| 2012/0032319 A1 | 2/2012 | Dunipace |
| 2012/0035578 A1 | 2/2012 | Yamanaka et al. |
| 2012/0141128 A1 | 6/2012 | Bai et al. |
| 2012/0277713 A1 | 11/2012 | Raycheck |
| 2012/0316526 A1 | 12/2012 | Rosati et al. |
| 2012/0316528 A1 | 12/2012 | Kreuzer et al. |
| 2012/0323195 A1* | 12/2012 | Ehrnsperger ........ A61F 13/5323 604/366 |
| 2013/0079740 A1* | 3/2013 | Ehrnsperger ............ A61L 15/22 604/370 |
| 2013/0110065 A1 | 5/2013 | Takahashi |
| 2013/0116644 A1 | 5/2013 | Wei et al. |
| 2013/0137274 A1 | 5/2013 | Takahashi |
| 2013/0331806 A1* | 12/2013 | Rosati ............... A61F 13/53743 604/366 |
| 2014/0005622 A1* | 1/2014 | Wirtz ................... A61F 13/532 604/366 |
| 2014/0005623 A1* | 1/2014 | Wirtz ................... A61F 13/539 604/366 |
| 2014/0068839 A1 | 3/2014 | Steele et al. |
| 2014/0107605 A1 | 4/2014 | Schroer et al. |
| 2014/0121487 A1* | 5/2014 | Faybishenko ..... A61F 13/15723 600/365 |
| 2014/0142528 A1 | 5/2014 | Wang et al. |
| 2014/0142529 A1 | 5/2014 | Cheng |
| 2014/0155856 A1 | 6/2014 | Rönnberg et al. |
| 2014/0163501 A1 | 6/2014 | Ehrnsperger et al. |
| 2014/0163503 A1 | 6/2014 | Arizti et al. |
| 2014/0221956 A1 | 8/2014 | Martynus et al. |
| 2014/0303589 A1 | 10/2014 | Paz et al. |
| 2014/0336605 A1 | 11/2014 | Hardie et al. |
| 2014/0345034 A1 | 11/2014 | Hansson et al. |
| 2014/0350508 A1 | 11/2014 | Popp et al. |
| 2014/0371701 A1 | 12/2014 | Bianchi et al. |
| 2015/0045759 A1 | 2/2015 | Martynus et al. |
| 2015/0045760 A1 | 2/2015 | Martynus et al. |
| 2015/0045761 A1 | 2/2015 | Martynus et al. |
| 2015/0051510 A1 | 2/2015 | Husmark et al. |
| 2015/0065973 A1 | 3/2015 | Roe et al. |
| 2015/0088086 A1 | 3/2015 | Beck |
| 2015/0157251 A1* | 6/2015 | Nelson ............... A61F 13/15585 600/362 |
| 2015/0173968 A1 | 6/2015 | Joseph |
| 2015/0209195 A1 | 7/2015 | Martynus et al. |
| 2015/0223996 A1 | 8/2015 | Martynus et al. |
| 2015/0257946 A1 | 9/2015 | Martynus et al. |
| 2015/0273793 A1 | 10/2015 | Thomas |
| 2015/0282997 A1 | 10/2015 | Arizti |
| 2015/0282998 A1* | 10/2015 | Arizti ................ A61F 13/51108 604/385.101 |
| 2015/0282999 A1 | 10/2015 | Arizti |
| 2015/0313770 A1 | 11/2015 | Hubbard et al. |
| 2016/0038350 A1 | 2/2016 | Martynus et al. |
| 2016/0278992 A1 | 9/2016 | Martynus et al. |
| 2016/0278993 A1 | 9/2016 | Martynus et al. |
| 2016/0278994 A1 | 9/2016 | Martynus et al. |
| 2016/0303275 A1 | 10/2016 | Joseph |
| 2017/0003257 A1 | 1/2017 | Klofta et al. |
| 2017/0246052 A1* | 8/2017 | Ludwig ............. A61F 13/49058 |
| 2017/0252015 A1* | 9/2017 | Barnhorst ......... A61F 13/49011 |
| 2018/0368817 A1 | 12/2018 | Tally et al. |
| 2018/0369029 A1* | 12/2018 | Barnhorst ............. A61F 13/535 |

FOREIGN PATENT DOCUMENTS

| | | |
|---|---|---|
| ES | 1170784 | 2/2017 |
| FR | 122985 A | 9/1960 |
| FR | 1229858 A | 9/1960 |
| FR | 77546 E | 3/1962 |
| JP | H 10295723 A | 11/1998 |
| KR | 1020100086255 A | 1/2009 |
| WO | WO199856327 | 12/1998 |
| WO | WO09155265 | 12/2009 |
| WO | WO2016122152 | 8/2016 |

OTHER PUBLICATIONS

All Office Actions for U.S. Appl. No. 16/002,244.
All Office Actions for U.S. Appl. No. 16/016,973.
All Office Actions for U.S. Appl. No. 15/446,077.
Print of page bearing heading "Marian Medical, Inc.," and bearing date Aug. 11, 2013 (2 pages), found at: http://webarchive.org/web/20130811003952/http://marianmedicalonline.com/products/ditty-diaper. No admission of relevance, materiality, prior art status or any other legal question is intended by this disclosure.
Print of page bearing heading "Marian Medical, Inc.," and bearing date Feb. 13, 2017 (2 pages), found at: http://marianmedicalonline.com/products/ditty-diaper/#. No admission of relevance, materiality, prior art status or any other legal question is intended by this disclosure.
PCT International Search Report, dated Jun. 7, 2017 (13 pages).
U.S. Appl. No. 16/016,973, filed Jun. 25, 2018, Jacob Alan Barnhorst et al.
All Office Actions; U.S. Appl. No. 17/458,638, filed Aug. 27, 2021.
All Office Actions; U.S. Appl. No. 17/463,580, filed Sep. 1, 2021.
U.S. Unpublished U.S. Appl. No. 17/458,638, filed Aug. 27, 2021, to Jacob Alan Barnhorst et al.
U.S. Unpublished U.S. Appl. No. 17/463,580, filed Sep. 1, 2021, to Jacob Alan Barnhorst et al.

* cited by examiner

DIAPER ADAPTED FOR COLLECTION OF UNCONTAMINATED AND INTACT STOOL SAMPLE FROM AN INFANT

CROSS REFERENCE TO RELATED APPLICATION

This application claims the benefit of U.S. Provisional Application No. 62/301,679, filed Mar. 1, 2016, the substance of which is incorporated herein by reference.

BACKGROUND OF THE INVENTION

Collection of stool samples from infants is sometimes desired for medical diagnostic or research purposes, for example, to identify or study characteristics or effects of medical conditions such as infections, allergies or other conditions. Typically in such circumstances it is desired to obtain a stool sample that is uncontaminated and intact, i.e., has not been contaminated by urine or any other substance, and has not had any of its constituents removed by, e.g., absorption into a diaper.

In a young infant, a bowel movement is usually not sufficiently predictable to provide warning or time for a caregiver to prepare to collect an uncontaminated and intact stool sample immediately after elimination occurs. An attempt at collection some period of time after elimination substantially increases the risk that the sample will be non-representative. Anticipatory methods and devices for stool sample collection used to date have included undesirably invasive devices and steps, e.g., use of catheters or bag devices, or have been deemed difficult, messy, hazardous and/or unreliable. Additionally, devices such as bag devices have often involved use of adhesive to affix them to the patient's skin. Particularly for premature and very young infants this may be unsatisfactory because these patients typically have very sensitive and delicate skin, which can be painfully irritated and even damaged by use of adhesives.

Disposable diapers of conventional design are unsuitable as stool sample collection devices because they are designed to rapidly absorb and retain liquid exudates in an absorbent structure.

Any stool in a conventional diaper that remains unabsorbed upon removal of the diaper from the infant will have had much of its liquid content removed by absorption into the absorbent structure, rendering it non-representative of its original composition.

Thus, there is room for improvement to methods and devices by which uncontaminated and intact stool samples may be collected from infants purposes of medical diagnosis, research, etc.

DESCRIPTION OF EXAMPLES

Definitions

Figure 1:
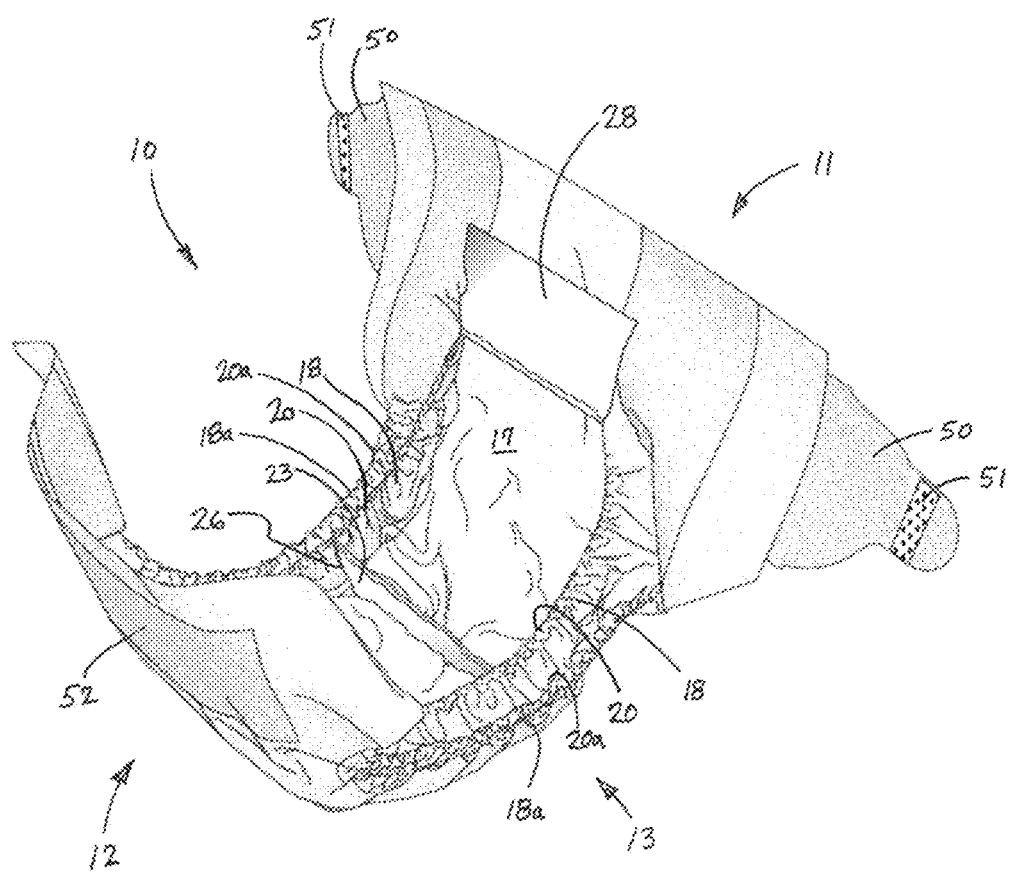
FIG. 1 is a perspective view of a diaper in a relaxed, opened position as it might appear resting on a table, wearing-facing side up.

The "liquid control structure" of a diaper includes all components and structure disposed between a liquid impermeable backsheet and a wearer-facing (wearer-contacting) layer, and disposed along the longitudinal axis of the diaper. An absorbent core structure as typically appears in currently marketed disposable diapers can be one type of "liquid control structure" as the latter term is used herein; however, a "liquid control structure" as the term is more broadly used herein may retainably absorb aqueous liquid, as a typical absorbent core structure, or may, alternatively, be adapted not to, or have a portion adapted not to, retainably absorb aqueous liquid. The liquid control structure of a diaper has a plan surface area when the diaper is laid out in extended and flat configuration on a horizontal surface, viewed from above along a direction orthogonal to the surface. The plan surface area also defines a volume of space, coextensive with the plan surface area in the x-y plane and quantified by the plan surface area and the average z-direction caliper or thickness of the liquid control structure.

"Lateral," "transverse," and forms thereof, with respect to a diaper or a component thereof, refers to a direction generally parallel to the waist edges of the diaper.

"Length," with respect to a diaper or a component thereof, refers to a dimension measured along a direction generally perpendicular to the waist edges of the diaper.

"Longitudinal," and forms thereof, with respect to a diaper or a component thereof, refers to a direction generally perpendicular to the waist edges of the diaper.

"Width," with respect to a diaper or a component thereof, refers to a dimension measured along a direction generally parallel to the waist edges of the diaper.

"Feces impermeable," with respect to a sheet or layer component of a diaper positioned to receive fecal material, means that liquid fecal material will not pass through the sheet or layer from one side to the other, without application of an amount of pressure, exceeding atmospheric level, to the liquid as it contacts the sheet or layer. A feces impermeable sheet or layer of material may be formed of a continuous, unapertured and non-porous polymer film; or a polymer film with apertures or pores that are sufficiently small in combination with sufficient surface properties of the polymer such that liquid fecal material will not pass through the apertures or pores without application of pressure; or a fibrous nonwoven web material having a combination of sufficiently small interstitial/interfiber spaces or pores and sufficient surface properties of the fibers such that liquid fecal material will not pass through the apertures or pores without application of pressure. An apertured or porous sheet or layer of material may be feces impermeable as defined above, but may be permeable to water vapor.

"Urine impermeable," with respect to a sheet or layer component of a diaper positioned to receive urine, means that the urine will not pass through the sheet or layer from one side to the other, without application of an amount of pressure, exceeding atmospheric level, to the urine as it contacts the sheet or layer. A urine impermeable sheet or layer of material may be formed of a continuous, unapertured and non-porous polymer film; or a polymer film with apertures or pores that are sufficiently small in combination with sufficient hydrophobic surface properties of the polymer such that urine will not pass through the apertures or pores without application of pressure; or a fibrous nonwoven web material having a combination of sufficiently small interstitial/interfiber spaces or pores and sufficient hydrophobic surface properties of the fibers such that urine will not pass through the apertures or pores without application of pressure. An apertured or porous sheet or layer of material may be urine impermeable as defined above, but may be permeable to water vapor.

"Urine permeable," with respect to a sheet or layer component of a diaper positioned to receive urine, means that urine will pass through the sheet or layer from one side to the other, without application of an amount of pressure, exceeding atmospheric level, to the urine as it contacts the sheet or layer. A urine permeable sheet or layer of material may be formed of a polymer film, having apertures or pores that are sufficiently large, and/or having sufficiently hydrophilic surface properties, such that urine will pass through the apertures or pores without application of pressure. A urine permeable sheet or layer of material may be formed of a fibrous nonwoven web material, having sufficiently large apertures, interstitial/interfiber spaces or pores, and/or having sufficiently hydrophilic surface properties of the fibers, such that urine will pass through the apertures or interstitial/interfiber spaces or pores without application of pressure.

"Inboard" and "outboard" are relative terms relating the locations of two features of a diaper with respect to a longitudinal axis of the diaper. A first feature of a diaper is inboard of a second feature of the diaper, and the second feature is outboard of the first feature, when the first feature lies closer to the longitudinal axis of the diaper than the second feature.

"Underlie" and "overlie" (and forms thereof) refer to a vertical positional relationship between two components of a diaper that is open, extended and laid out flat on a horizontal surface with the wearer-facing surfaces facing up. With the diaper in this position, a first component overlies a second component, and the second component underlies the first component, when the first component lies directly or indirectly over or on top of the second component, or the second component lies directly or indirectly beneath the first component.

The terms "upper" and "lower," and forms thereof, used with respect to components of a diaper, relate to the vertical direction and positioning of the components when the diaper is open, extended and laid out flat on a horizontal surface with the wearer-facing surfaces facing up. With respect to FIGS. 5, 6 and 8, the uppermost components depicted are nearest the top of the page and the lowermost components are nearest the bottom of the page.

Figure 4A:
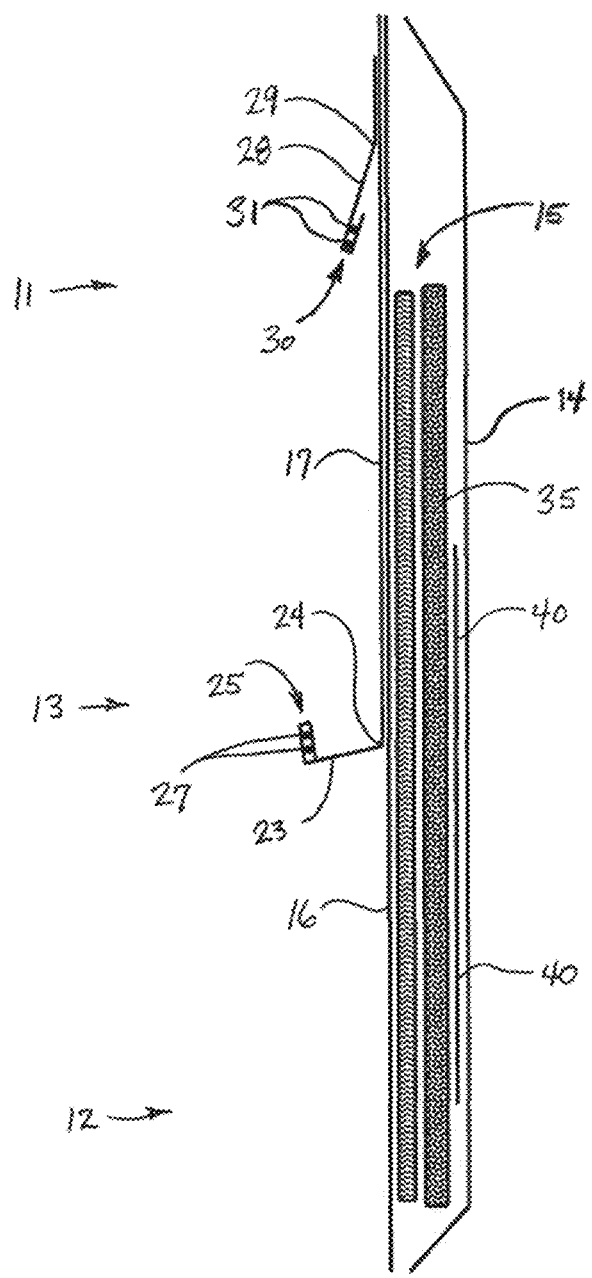
FIG. 4A is a schematic, exploded longitudinal cross-section of one example of the diaper shown in FIG. 2, taken along line 4-4 shown in FIG. 2.
Figure 4B:
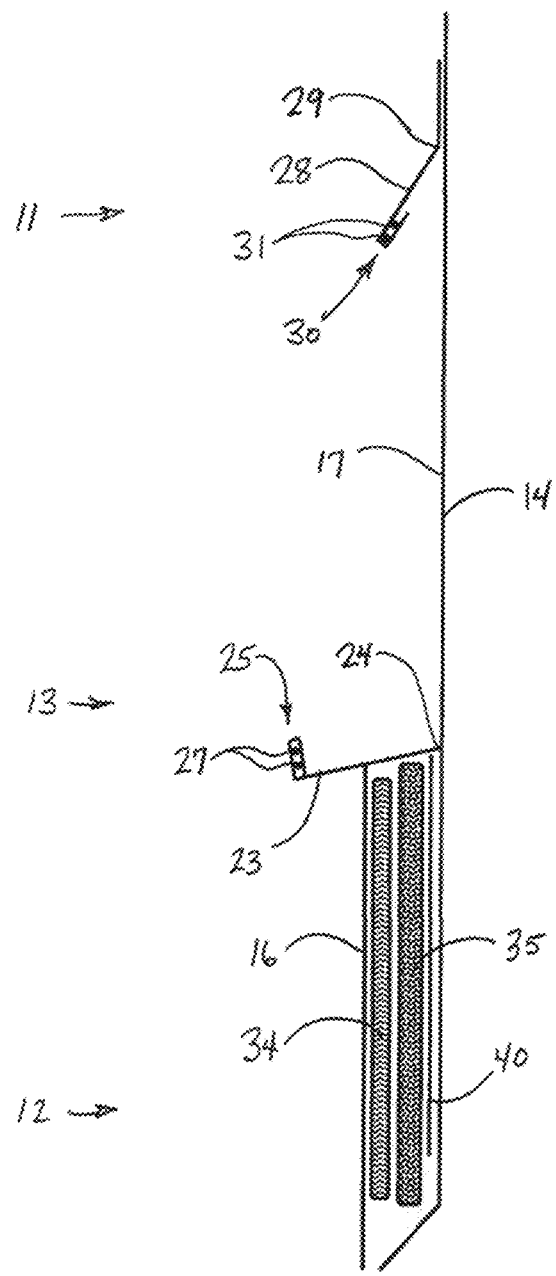
FIG. 4B is a schematic, exploded longitudinal cross-section of another example of the diaper shown in FIG. 2, taken along line 4-4 shown in FIG. 2.
Figure 5:
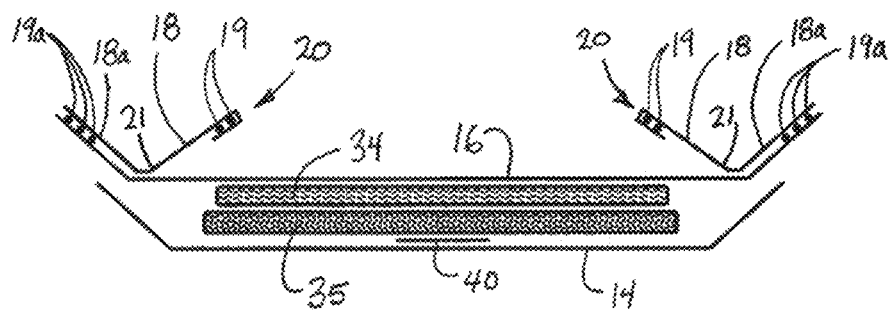
FIG. 5 is a schematic, exploded lateral cross-section of one example of the diaper shown in FIG. 2, taken along line 5-5 shown in FIG. 2.
Figure 6:
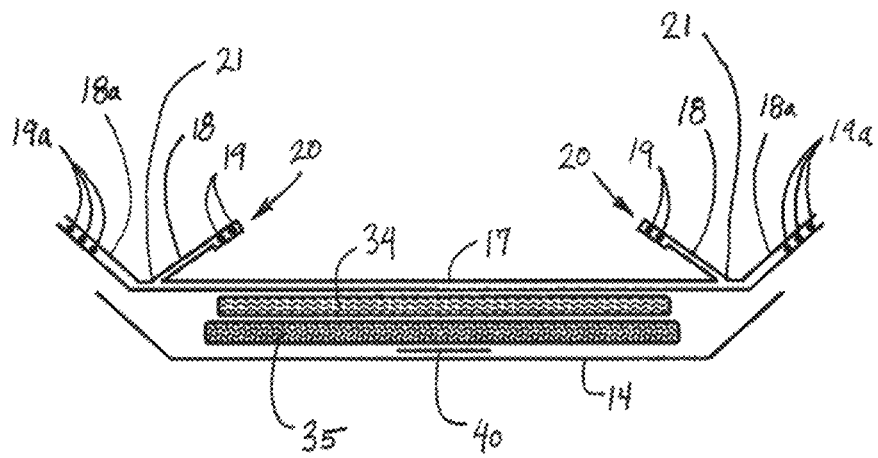
FIG. 6 is a schematic, exploded lateral cross-section of one example of the diaper shown in FIG. 2, taken along line 6-6 shown in FIG. 2.
Figure 8:
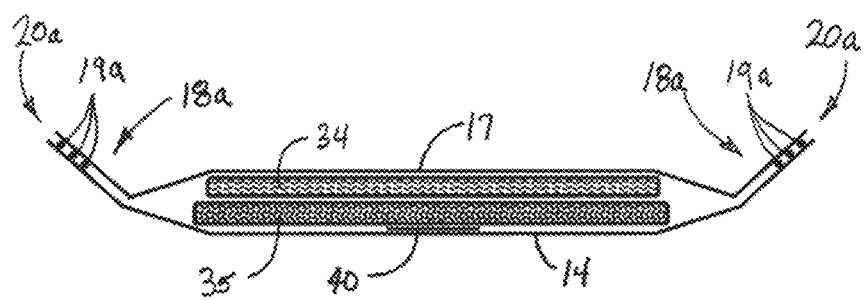
FIG. 8 is a schematic, exploded lateral cross-section of the diaper shown in FIG. 7, taken along line 8-8 shown in FIG. 7.

"Wearer-facing," with respect to a diaper or a component thereof, means the side of the diaper or component that faces the wearer's body when the diaper is worn in its normal configuration, with the backsheet to the outside. "Outward-facing" means the side of the diaper or component that faces away from the wearer when the diaper is worn in its normal configuration. In FIGS. 4A and 4B, the wearer-facing side of each component depicted is to the left, and the outward-facing side of each component is to the right. In FIGS. 5, 6 and 8, the wearer-facing side of each component depicted is toward the top of each figure, and the outward-facing side is toward the bottom.

"x-y plane", used with respect to a diaper, relates to a plane parallel to a horizontal surface upon which the diaper may be opened, extended and laid out flat with the wearer-facing surfaces facing up. With respect to FIGS. 2, 3 and 7, the plane of the page is an x-y plane.

"z-direction," used with respect to a diaper, relates to the direction orthogonal to a horizontal surface defining a plane upon which the diaper may be opened, extended and laid out flat with the wearer-facing surfaces facing up. With respect to FIGS. 2, 3 and 7, the z-direction is the direction orthogonal to the plane of the page.

Description

Figure 2:
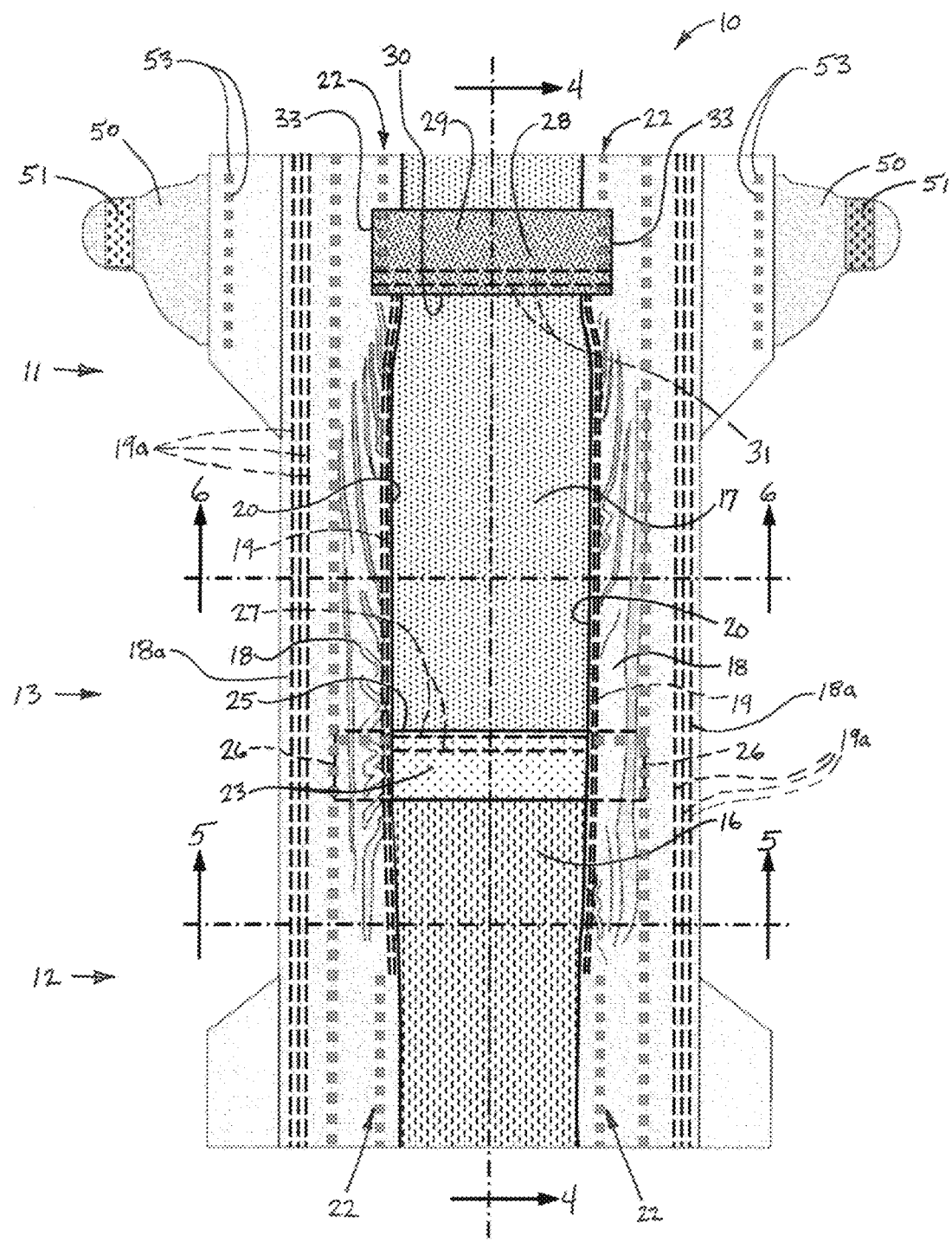
FIG. 2 is a plan view of a diaper in an extended and flat condition, with the wearer-facing surfaces facing the viewer.
Figure 3:
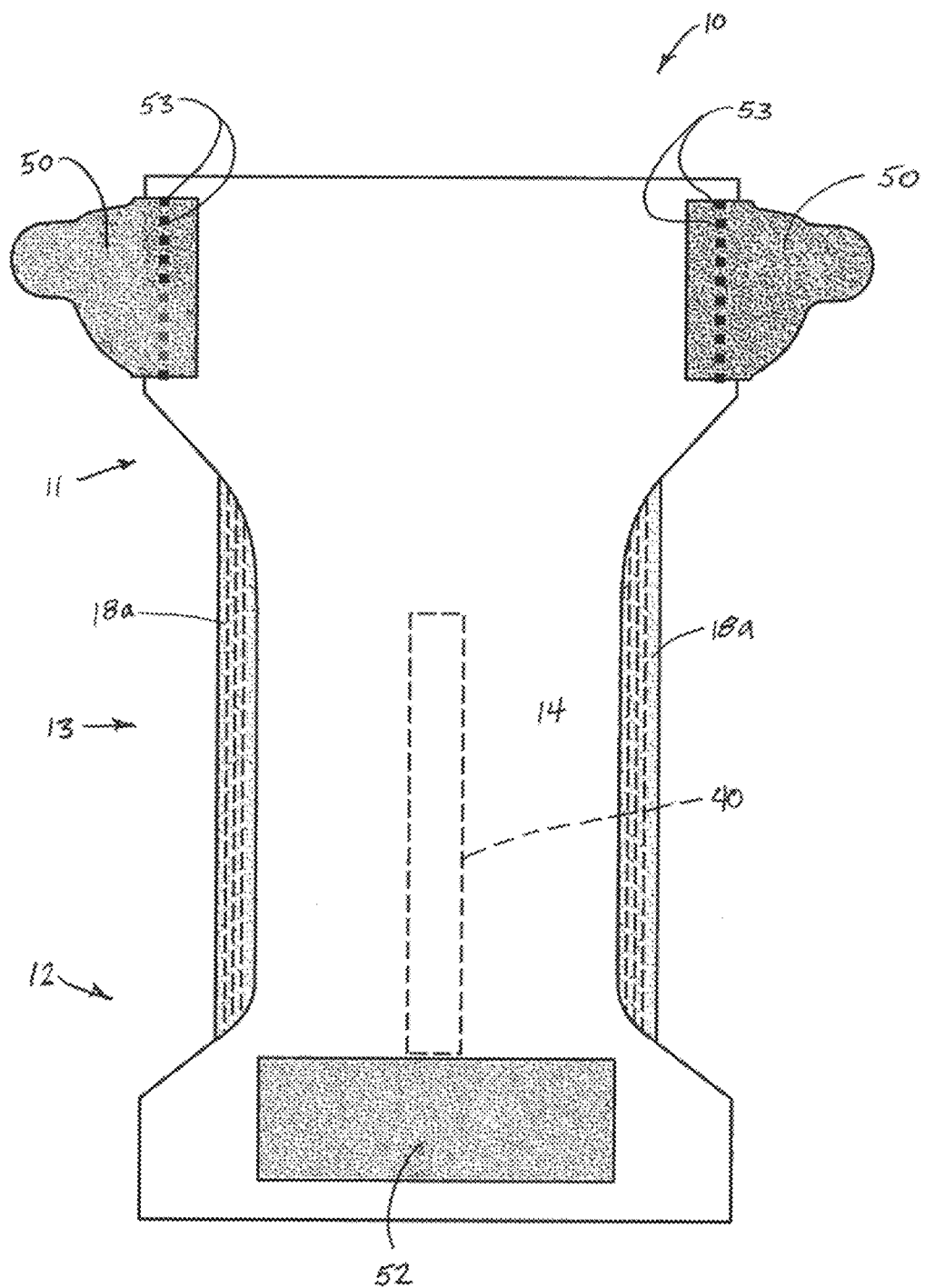
FIG. 3 is a plan view of a diaper in an extended and flat condition, with the outward-facing surfaces facing the viewer.

FIGS. 1-8 depict various features of the invention that may be embodied in a diaper 10. Diaper 10 may have a rear portion 11, front portion 12 and perineal portion 13 between the front portion and rear portion. For reference, the lateral width of diaper 10 may be equally divided lengthwise by an imaginary longitudinal axis 4-4 (FIG. 2).

Diaper 10 may including a pair of fastening members 50 extending laterally outboard of the main structure in the rear portion 11. Fastening members 50 may be integral and/or contiguous with other components forming the diaper (such as the backsheet and/or topsheet), or may be separately formed and attached via bonds 53 as suggested in FIGS. 2 and 3. Fastening members 50 may be formed of a nonwoven web material, a polymer film material (which may be elastomeric), a laterally elastically stretchable stretch laminate material, or any other web/sheet material having lateral tensile strength suitable for sustaining lateral tensile forces present when the diaper is fastened about an intended wearer. Each fastening member may have affixed thereon a fastening component 51 such as a patch of hooks, forming a component of a hook-and loop fastening system; alternatively, fastening component 51 may be a patch of material bearing adhesive, or any other suitable fastening mechanism. A corresponding receiving material such as patch of loops material or adherent material that effectively contacts and fastenably attaches to the adhesive-bearing material may be included on the outer side of front portion 12 of the diaper at a landing zone 52. It will be appreciated that other types of fastening components and fastening systems are known and may be used as an alternative to a hook-and-loop or adhesive fastening system.

Backsheet

Diaper 10 may have an outer backsheet 14 that forms most of the outward-facing surfaces of the diaper when worn. Backsheet 14 may be urine and feces impermeable and may be formed of a single layer of material or may be formed of a laminate of two or more layers of material. In one example, backsheet 14 may be formed of an inner layer of an effectively urine and feces impermeable polymeric film, laminated with an outer layer of a nonwoven web material. In a more simple example, backsheet 14 may be formed of a layer of polymeric film alone.

In disposable diapers, it is often desired that the backsheet have high opacity, for aesthetic purposes of concealment of the presence of exudates contained in the diaper. However, for purposes of timely collection of a sample, in some examples it may be desired that the backsheet have sufficient translucency to enable easy visual detection of the presence of stool and/or urine therein. Manipulation of opacity (conversely, translucency) by selection of material components and manufacturing techniques is well known in the art. It may be desired that the backsheet have an opacity of no greater than 50 percent, more preferably no greater than 45 percent, even more preferably no greater than 40 percent, and still more preferably no greater than 35 percent, as measured by the opacity test method described below.

Front and Rear Topsheets

Diaper 10 may include a liquid control structure 15 adapted to receive, absorb and retain liquid exudates (e.g., urine). As may be seen in FIGS. 4A-6, liquid control structure 15 may be disposed in the diaper between backsheet 14, and a front topsheet 16 in the front portion 12, and a rear topsheet 17 in the rear portion 11.

The front topsheet 16 may be formed of a urine permeable material, for example, a nonwoven material such as described in U.S. Pat. No. 8,968,614. For purposes of ensuring rapid passage of urine through the front topsheet 16 to the materials of the liquid control structure 15, thereby minimizing chances of contamination of a stool sample with urine, it may be desired that the front topsheet 16 be formed of an apertured nonwoven material formed of fibers. The fiber constituents may be selected or manufactured to be inherently hydrophilic, or may be treated, e.g., with an application of a surfactant, to impart hydrophilic surface properties. Suitable examples of apertured topsheets are described in U.S. Pat. Nos. 7,033,340; 6,680,422; 6,498,284; 6,414,215; 5,516,572; and 5,342,338; and in pending U.S. application Ser. No. 14/270,468.

The rear topsheet 17 may be formed of an effectively feces impermeable material that hinders or blocks passage of liquid constituents therethrough. In one example, rear topsheet 17 may be formed of a polymeric film. In another example, rear topsheet 17 may be formed of an effectively feces impermeable nonwoven web material. An example of such material is disclosed in, for example, U.S. Pat. App. Pub. No. 2006/0014460.

For purposes of simplification of manufacturing, it may be desired that the material forming a urine permeable front topsheet 16 extends to the rear portion of the diaper, or even the full length of the diaper 10. This eliminates the need for special cutting and/or material bonding steps that would be associated with including a foreshortened front topsheet 16, i.e., one that does not extend the full length of the diaper. If a full-length front topsheet 16 is included, it may be simply overlaid by the effectively liquid-impermeable rear topsheet 17.

In another example, one contiguous sheet of material may be used to form both front topsheet 16 and rear topsheet 17. The material may manufactured or treated to be effectively urine permeable in the front portion 12 and effectively feces impermeable in the rear portion 11. In one particular example, an effectively feces impermeable material may form a single contiguous layer constituting both front topsheet 16 and rear topsheet 17, but the material may be subjected to an aperturing process that forms apertures in the front portion, making the front topsheet 16 portion effectively urine permeable. In another particular example, an effectively urine permeable material may form a single contiguous layer constituting both front topsheet 16 and rear topsheet 17, but the material may be subjected to a process rendering it effectively feces impermeable in the rear portion. Suitable processes may include applying a film layer to the rear portion; applying a melted hydrophilic polymer composition to the rear portion by methods such as slot coating or roller techniques such as used in printing; spraying a hydrophilic coating material (such as, for example, a wax) over the material of the rear portion, etc.

In another more simple example, the rear topsheet 17 and the backsheet 14 may be integral and/or unitary in the rear portion of the diaper, behind the transverse perineal barrier 23 (described below). In other words, a single, effectively feces impermeable web member or a single, effectively feces impermeable multi-layer laminate, may form both the outward-facing surface of the diaper and the wearer-facing surface of the diaper, in the rear portion of the diaper, with no separate intermediate layer. In such example, the components of the liquid control structure may be disposed only in the portion of the diaper forward of the transverse perineal barrier 23. This example is illustrated schematically in FIG. 4B.

Longitudinal Cuffs

Diaper 10 may include a pair of standing longitudinal cuffs 18. Such cuffs are currently common in disposable diapers and are variously known as gasketing cuffs, standing cuffs, barrier cuffs, etc. Longitudinal cuffs 18 may be formed of a fibrous nonwoven material, a polymeric film material, or a laminate thereof. In one example, longitudinal cuffs 18 may be formed of an effectively feces impermeable material, which will serve to prevent escape of liquid constituents of stool collected in the diaper. Non-limiting examples of suitable materials for forming longitudinal cuffs are described in U.S. Pat. No. 7,695,463.

Longitudinal cuffs 18 may each have a proximal portion 21 affixed to an underlying component of the diaper structure such as a topsheet and/or backsheet, and a free longitudinal distal edge 20. Each cuff 18 may be longitudinally affixed along the proximal portion 21 to the diaper structure by mechanical or thermal bonding, by adhesive or other means, or a combination thereof, however, use of adhesive to bond or supplementally bond proximal portions 21 to the structure may serve to provide a liquid seal at the junction between the cuff 18 and the underlying component. In one example, the proximal portion 21 of the cuff 18 is bonded to the rear topsheet 17 with a continuous application of adhesive therebetween, to provide a liquid seal at the junction. The adhesive may be a hot-melt type adhesive conventionally used in the manufacture of disposable diapers.

As may be appreciated from FIG. 2, the material forming longitudinal cuffs 18 and the free distal edges 20 thereof may additionally be bonded to the diaper structure at cuff edge/end bonds 22. In combination, cuffs 18 may each include one or more longitudinal cuff elastic members 19 proximate the free longitudinal distal edges 20. During manufacturing, longitudinal cuff elastic members 19 may be incorporated and affixed into the cuff 18 structures in a pre-strained condition. Upon completion of manufacturing, release from the manufacturing line, and relaxation of the diaper structure, the elastic members 19 longitudinally contract toward their unstrained lengths, causing the free edges 20 to pull longitudinally against the cuff end/edge bonds 22, thereby causing the diaper 10 structure to curl toward the wearer-facing side as suggested in FIG. 1, and causing the free edges 20 of the cuffs to pull away from the structure and the cuffs to "stand." This feature causes the free edges 20 of the cuffs to extend toward and draw against the wearer's skin along the buttocks and through the crotch region, when the diaper is worn, thereby performing a gasketing function that serves to contain exudates between the cuffs 18.

This combination of cuff end/edge bonds 22 and pre-strained longitudinal cuff elastic members 19 can cause the cuffs 18 to stand as described above regardless of whether the edges 20 and end/edge bonds 22 are disposed inboard, or outboard, of the affixed proximal portions 21 of the cuffs. In the example depicted in FIGS. 2, 4 and 5, it can be appreciated that the location of end/edge bonds 22 relative affixed proximal portions 21 causes the free edges 20 of cuffs 18, while standing, to be drawn by contraction of elastic members 19 toward the center of the diaper (i.e., toward longitudinal axis 4-4). This may cause free edges 20 to tend to rest against areas of the wearer's crotch region closer to the longitudinal center of the diaper when the diaper is worn. In another example, however, cuffs 18 may be constructed such that end/edge bonds 22 are disposed outboard of the affixed proximal portions of the cuffs 18, such that free edges 20 of cuffs 18 are drawn by contraction of elastic members 19 away from the longitudinal axis 4-4, i.e., toward more outboard regions of the diaper. This may cause free edges 20 of cuffs 18 to tend to rest against the wearer's skin in locations more laterally removed from central areas in the wearer's crotch region, e.g., against the inward-facing surfaces of the buttocks in the gluteal cleft, and against the inner thighs in the crotch region. Better gasketing and better liquid containment may occur with one or the other configuration depending upon wearer size, position and activity level, and thus one or the other configuration may be preferred under given circumstances. Other non-limiting examples of suitable longitudinal cuff construction are described in U.S. Pat. No. 7,794,441.

Elastic members 19 may be discontinuously or continuously adhered along their lengths to the material(s) forming cuff 18 structures by, e.g., adhesive applied by strand-coating the elastic members. In some examples the material forming the cuffs 18 may be folded over the elastic members 19 to better contain them and restrain them within the structure in the event of failure of the adhesive. This has the further advantage of providing a folded (rather than cut) material edge as distal edge 20, providing a neat appearance and softer feel.

In some examples it may be desired that rear topsheet 17 and longitudinal cuffs 18 are continuously integrally joined where they meet, thereby preventing escape of liquid at the junction therebetween. In one example suggested in FIG. 6, an effectively liquid impervious sheet or web material (such as a polymer film) forming rear topsheet 17 in whole or in part may contiguously form a portion or layer of each longitudinal cuff 18 in the rear portion of the diaper.

Figure 7:
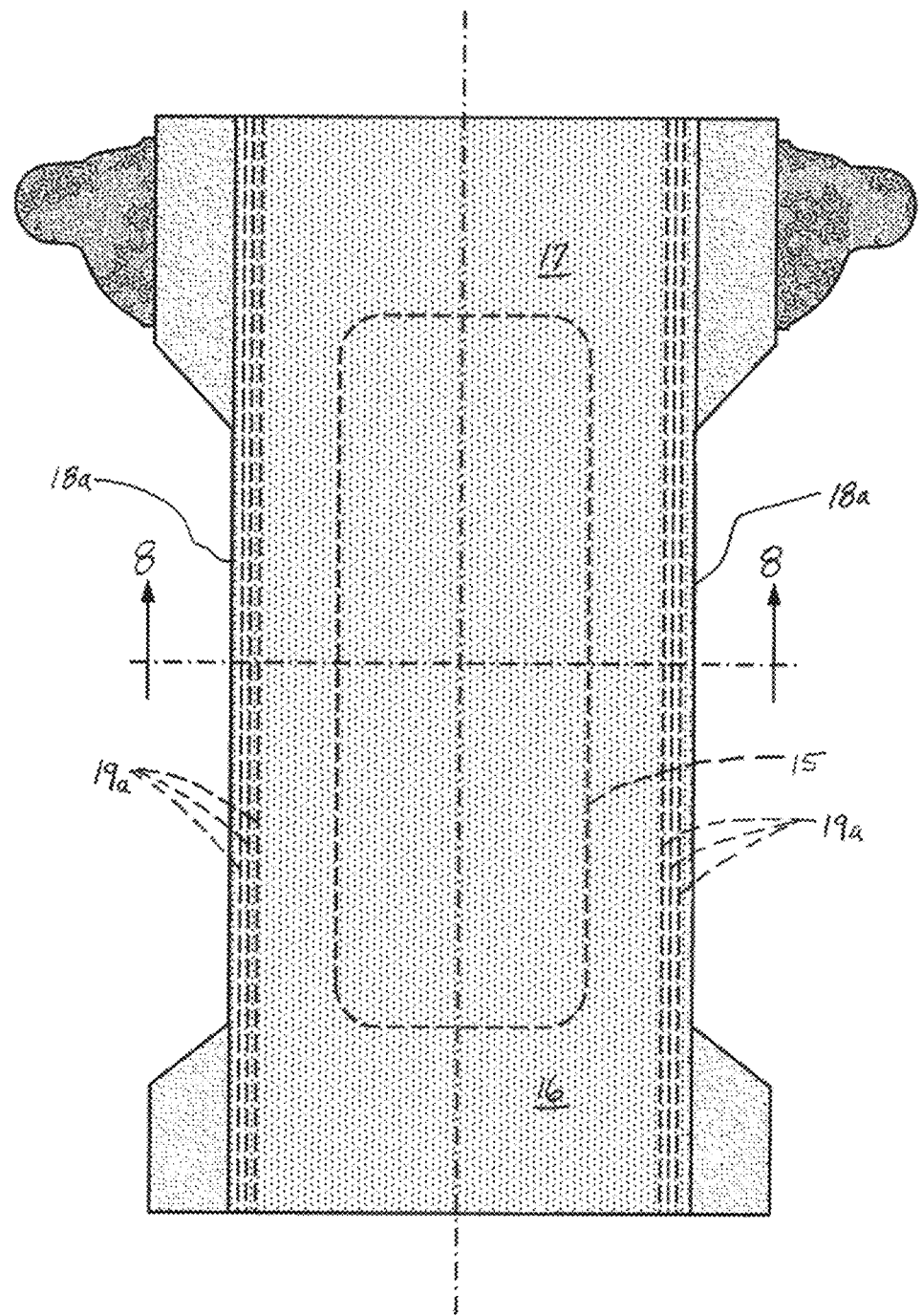
FIG. 7 is a plan view of another example of a diaper in an extended and flat condition, with the wearer-facing surfaces facing the viewer.

In a simplified example made more apparent in FIGS. 7 and 8, longitudinal outer cuffs 18a may be formed by an alternative and/or additional configuration by portion(s) of the material of the topsheet 16, 17 and/or backsheet 14 extending laterally beyond the liquid control structure 15, with attached, sandwiched, enveloped or otherwise captured outer cuff elastic members 19a. Outer cuff elastic members 19a may also be incorporated into the structure while in a pre-strained condition as described above. Upon completion of manufacturing, release from the manufacturing line, and relaxation of the diaper structure, the elastic members 19a longitudinally contract toward their unstrained lengths, causing the free edges 20a to pull longitudinally, thereby causing the diaper 10 structure to curl toward the wearer-facing side as suggested in FIG. 1, and causing the free edges 20a of the cuffs to lift up from the structure and the outer cuffs to "stand". This feature causes the free edges 20a of the outer cuffs to draw against the wearer's skin along the inner thighs and buttocks, when the diaper is worn, thereby performing a gasketing function that serves to contain exudates within the diaper.

In another example apparent in FIGS. 1, 2, 5 and 6, a diaper may be configured with two pairs of longitudinal cuffs, longitudinal cuffs 18, and outer longitudinal outer cuffs 18a.

Transverse Perineal Barrier

As reflected in FIGS. 1, 2 and 4, diaper 10 may include a transverse perineal barrier 23. Transverse perineal barrier 23 may be disposed in the perineal portion 13 of the diaper, suitably located to extend transversely across the diaper, between the anus and genitals of the wearer when the diaper is worn. A single diaper design may be manufactured with a transverse perineal barrier in a location suitable for both male and female wearers. Alternatively, a selection of at least two differing designs may be manufactured (and offered for sale at retail in an array), one for male wearers and one for female wearers. The two designs may differ in, at least, the location of the transverse perineal barrier, with one design having the perineal barrier in a location more closely suited to male wearer anatomy, and the other design having the perineal barrier in a location more closely suited to female wearer anatomy.

Transverse perineal barrier 23 may have a proximal portion 24 and a free distal edge 25. Free distal edge 25 of perineal barrier 23 may bridge respective free distal edges 20 of left and right standing longitudinal cuffs 18 or outer longitudinal cuffs 18a.

Transverse perineal barrier 23 may be formed of an effectively urine and feces impermeable material. In one example, it may be formed of a polymer film. In another example, it may be formed of an effectively urine and feces impermeable fibrous nonwoven web material, or a laminate of a polymer film and a fibrous nonwoven web material. In one example, perineal barrier 23 may be formed of the same type material as longitudinal cuffs 18.

Transverse perineal barrier 23 may be transversely affixed along the proximal portion 24 to an underlying component of the diaper structure by mechanical or thermal bonding, by adhesive or other means, or a combination thereof, however, use of adhesive to bond or supplementally bond proximal portion 24 to the structure may serve to provide a liquid seal at the junction between the barrier 23 and the diaper structure. In one example, proximal portion 24 of the barrier 23 is bonded to the rear topsheet 17 with a continuous application of adhesive therebetween, to provide a liquid seal at the junction. The adhesive may be a hot-melt type adhesive conventionally used in the manufacture of disposable diapers.

In some examples it may be desired that rear topsheet 17 and perineal barrier 23 are continuously integrally joined where they meet, thereby preventing escape of liquid at the junction therebetween. In one example suggested in FIG. 4A, an effectively liquid impervious sheet or web material (such as a polymer film) forming rear topsheet 17 in whole or in part may contiguously form a portion or layer of perineal barrier 23. It may also be desired that side edges 26 of perineal barrier 23 are continuously integrally joined to the material forming longitudinal cuffs 18, thereby preventing escape of liquid at a junction therebetween.

Transverse perineal barrier 23 may be manufactured to have a substantially straight free distal edge 25 and may also include one or more perineal barrier elastic members 27. In a manner similar to inclusion of longitudinal cuff elastic members 19, during manufacturing, perineal barrier elastic members 27 may be incorporated and affixed into the barrier 23 structure in a pre-strained condition. Upon completion of manufacturing, release from the manufacturing line, and relaxation of the diaper structure, the elastic members 27 contract toward their unstrained lengths, causing the free distal edge 25 of barrier 23 to pull transversely against the respective free distal edges 20 of the longitudinal cuffs. When the longitudinal cuffs 18 "stand" as described above, this causes the perineal barrier 23 also to "stand". This feature causes the free distal edge 25 of the perineal barrier 23 to draw toward the wearer's skin across the perineum, when the diaper is worn, thereby performing a gasketing function that serves to prevent passage of liquid exudates between the cuffs 18 from the rear portion of the diaper 11 to the front portion of the diaper 12, and vice versa. Thus, urine exudate in the front of the diaper may be prevented from contaminating stool exudate contained in the rear portion of the diaper, and liquid constituent of stool exudate may be prevented from moving to the front portion 12 of the diaper where it could pass through a urine permeable front topsheet 16 into the liquid control structure.

As suggested in FIGS. 4A and 4B, the transverse perineal barrier 23 may be configured such that a marginal portion proximate to distal edge 25 tends to bend over, which will cause it lay in a flat configuration against the wearer's skin when the diaper is worn. This may improve comfort of the diaper and reduce any tendency of the transverse barrier to chafe or mark the wearer's skin. In one example, elastic members 27 may be one or more flattened strips of elastomeric material (rather than round strands), which may further enhance the tendency of the marginal portion to bend and lay over flat against the wearer's skin. In one example, the marginal portion at left and right sides thereof may be attached to longitudinal cuffs along a direction that is not perpendicular to, or even substantially parallel to, to the free edges 20 of the cuffs, serving to urge the marginal portion into a bent-over configuration when the diaper is worn.

For purposes of maximizing a gasketing function pulling the cuffs and perineal barrier toward the wearer's skin, it may be desired that free distal edge 25 of transverse perineal barrier 23 is affixed to each longitudinal cuff 18 at a location within 5 mm or less, more preferably within 2 mm or less, of each free distal edge 20 of each longitudinal cuff 18. For the same purpose, and alternatively or in combination therewith, it may be desired that the perineal barrier 23 is configured such that at least one and preferably all of perineal barrier elastic members 27 are disposed with their ends or some portion proximate their ends no more than 5 mm or less, more preferably no more than 2 mm or less, of a longitudinal cuff elastic member 19. This helps create an effectively continuously elasticized, tailored gasketing structure that more closely fits the wearer's body in front and to the sides of the anus.

Transverse Rear Cuff

As reflected in FIGS. 1, 2 and 4, diaper 10 may include a transverse rear cuff 28. A transverse rear cuff 28 may help the rear portion 11 of the diaper more effectively contain highly liquid stool, particularly when discharged in rapid or forceful bowel movements.

Transverse rear cuff 28 may be disposed in the rear portion 11 of the diaper. Transverse rear cuff 28 may have a proximal portion 29 and a free distal edge 30. Free distal edge 30 of rear cuff 28 may bridge the respective free distal edges 20 of the left and right standing longitudinal cuffs 18.

Transverse rear cuff 28 may be formed of an effectively feces impermeable material. In one example, it may be formed of a polymer film. In another example, it may be formed of an effectively feces impermeable fibrous nonwoven web material, or a laminate of a polymer film and a fibrous nonwoven web material. In one example, rear cuff 28 may be formed of the same type material as longitudinal cuffs 18.

Transverse rear cuff 28 may be transversely affixed along the proximal portion 24 to the diaper structure by mechanical or thermal bonding, by adhesive or other means, or a combination thereof, however, use of adhesive to bond or supplementally bond proximal portion 24 to the structure may serve to provide a liquid seal at the junction between the barrier 23 and the diaper structure. In one example, proximal portion 29 of the rear cuff 28 is bonded to the rear topsheet 17 with a continuous application of adhesive therebetween, to provide a liquid seal at the junction. The adhesive may be a hot-melt type adhesive conventionally used in the manufacture of disposable diapers.

In some examples it may be desired that rear topsheet 17 and rear cuff 28 are continuously integrally joined where they meet, thereby preventing escape of liquid at the junction therebetween. In one example, an effectively liquid impervious sheet or web material (such as a polymer film) forming rear topsheet 17 in whole or in part may contiguously form a portion or layer of rear cuff 28. It may also be desired that side edges 33 of rear cuff 28 are continuously integrally joined to the material forming longitudinal cuffs 18, thereby preventing escape of liquid at a junction therebetween.

Transverse rear cuff 28 may be manufactured to have a substantially straight free distal edge 30 and may also include one or more rear cuff elastic members 31. In a manner similar to inclusion of longitudinal cuff elastic members 19, during manufacturing, rear cuff elastic members 31 may be incorporated and affixed into the rear cuff 28 structure in a pre-strained condition. Upon completion of manufacturing, release from the manufacturing line, and relaxation of the diaper structure, the elastic members 31 contract toward their unstrained lengths, causing the free distal edge 30 of rear cuff 28 to pull transversely against the respective free distal edges 20 of the longitudinal cuffs. When the longitudinal cuffs 18 "stand" as described above, this causes the rear cuff 28 also to "stand". This feature causes the free distal edge 30 of the rear cuff 28 to draw toward the wearer's skin above the wearer's gluteal cleft, when the diaper is worn, thereby performing a gasketing function that serves to prevent passage of liquid exudates between the cuffs 18 and out of the rear portion 11 of the diaper 10. Thus, liquid constituents of stool exudate may be prevented from escaping the diaper.

For purposes of maximizing a gasketing function pulling the distal edges 20 of longitudinal cuffs 18 and distal edge 30 of rear cuff 28 toward the wearer's skin, it may be desired that free distal edge 30 of transverse rear cuff 28 is affixed to each longitudinal cuff 18 at a location within 5 mm or less, more preferably within 2 mm or less, of each free distal edge 20 of each longitudinal cuff 18. For the same purpose, and alternatively or in combination therewith, it may be desired that the rear cuff 28 is configured such that at least one and preferably all of rear cuff elastic members 31 are disposed with their ends or some portion proximate their ends no more than 5 mm or less, more preferably no more than 2 mm or less, of a longitudinal cuff elastic member 19. This helps create an elasticized, tailored gasketing structure that more closely fits the wearer's body to the rear of the anus. In combination with the configuration of elastic members described above, a gasketing structure substantially entirely circumscribing the wearer's anus is thereby created.

Any one, combination of, or all, of the elastic members in the longitudinal cuffs, transverse perineal barrier and transverse rear cuff discussed above may be may be formed of strands (round-cross section) or strips (rectangular cross section) of elastomeric material. Suitable examples of elastomeric material include natural rubber strands as available from Easthampton Rubber Company of Stewart, Va., under the trademark L-1900 Rubber Compound; natural rubber elastic tape sold under the trademark Fulflex 9411 by Fulflex Company of Middletown, R.I.; polyurethane; and synthetic elastomers (e.g., LYCRA strands from Invista Corp., Wichita, Kans.).

Liquid Control Structure

As noted above, a urine permeable front topsheet 16, such as an apertured nonwoven front topsheet 16, which may be adapted to be hydrophilic, may be preferred.

Below the front topsheet 16, liquid control structure 15 is preferably configured to provide for rapid acquisition, distribution to absorbent components, and absorption of urine, quickly after a urination event. Rapid absorption of urine reduces the chance that urine may escape the front portion of the diaper to the rear portion of the diaper, and contaminate stool that may be present in, or later be discharged in, the rear portion.

Accordingly, it may be desired that the liquid control structure include an acquisition layer 34 beneath the front topsheet 16 and above an absorbent layer 35. Layer 34 may have the form of, e.g., a layer, mat or other body formed of or including, e.g., comminuted cellulose fibers, or other hydrophilic natural, semi-synthetic or synthetic fibers or other material that may be used to form a mat, layer or other body. Other suitable materials for forming an acquisition layer 34 are described in, for example, U.S. Pat. App. Pub. No. 2004/0158213

In one example, the acquisition layer 34 may include a nonwoven mat formed of fibers, which may be manufactured or adapted to be hydrophilic. In one example, acquisition layer 34 may include chemically cross-linked cellulosic fibers, which may or may not form part of a nonwoven material. In another example, acquisition layer 34 may include a nonwoven without the cross-linked cellulosic fibers. In another the acquisition layer may include chemically cross-linked cellulosic fibers mixed with other fibers such as natural or synthetic polymeric fibers. In some examples, such other natural or synthetic polymeric fibers may include high surface area fibers, thermoplastic binding fibers, polyethylene fibers, polypropylene fibers, PET fibers, rayon fibers, lyocell fibers, eucalyptus fibers and mixtures thereof. Suitable non-woven materials for the acquisition layer may include, but are not limited to, SMS material, including a spunbonded, a melt-blown and a further spunbonded layer. In certain examples, permanently hydrophilic nonwovens, and in particular, nonwovens with durably hydrophilic coatings are desirable. Another suitable example includes an SMMS-structure. In certain examples, the nonwovens are porous.

The absorbent layer 35 may be formed of any absorbent material that is generally compressible, conformable, non-irritating to the wearer's skin when positioned as shown and described herein, and capable of absorbing and retaining liquids such as urine. Absorbent layer 35 may comprise a wide variety of liquid-absorbent materials commonly used in disposable diapers and other absorbent articles such as comminuted wood pulp, which is generally referred to as air felt or fluff. Examples of other suitable absorbent materials include creped cellulose wadding; melt blown polymers, including co-form; chemically stiffened, modified or cross-linked cellulosic fibers; tissue, including tissue wraps and tissue laminates, absorbent open-celled foams (such as, for example, described in U.S. Pat. Pub. No. 2015/0313770), absorbent sponges, superabsorbent polymers (such as superabsorbent fibers), absorbent gelling materials, hydrogel-forming particles, or any other known absorbent material or combinations of materials. Examples of some combinations of suitable absorbent materials are cellulosic fiber fluff blended or interlaced with absorbent polymer particles, absorbent gelling materials and/or superabsorbent polymers, and absorbent gelling materials and super absorbent fibers etc. The storage layer may further comprise minor amounts (typically less than 10%) of non-liquid absorbent materials, such as adhesives, waxes, oils and the like. In some examples, the absorbent layer 35 may comprise materials and be configured as described in U.S. Patent Applications, Pub. Nos. US2014/0163511; US2014/0163503; US2014/0163501; US2014/0163500; US2012/0316526; US2012/0316528; US2014/0163501; and US2014/0371701.

The absorbent layer 35 may include absorbent polymer particles alone or in combination with other materials, such as cellulose fiber. The absorbent polymer particles may be immobilized on a substrate layer by, for example, a thermoplastic adhesive material. Absorbent polymer particles suitable for use in the absorbent layer may include any absorbent polymer particles known from superabsorbent literature, for example such as described in Modern Superabsorbent Polymer Technology, F. L. Buchholz, A. T. Graham, Wiley 1998. The absorbent polymer particles may be spherical, spherical-like, ellipsoid, or irregularly shaped, such as ovoid-shaped particles of the kind that may be obtained from inverse phase suspension polymerizations. The particles may, optionally, be agglomerated at least to some extent to form larger irregular agglomerations of particles. The absorbent polymer particles may be selected from among polyacrylates and polyacrylate based materials that are internally and/or surface cross-linked, such as for example partially neutralized cross-linked polyacrylates or acid polyacrylate. Examples of absorbent polymer particles suitable in the present disclosure are described for instance in U.S. Pat. No. 5,714,156, and PCT Patent Applications Nos. WO 07/047598, WO 07/046052, WO2009/155265 and WO2009/155264. In alternative examples, the absorbent layer may be substantially cellulose-free. (Herein, "substantially cellulose free" means that the absorbent layer has less than about 10 percent by weight cellulose fiber.) Airfelt and other cellulose fiber have been used as absorbent fillers in absorbent cores of disposable diapers. Such fiber possesses absorbent properties and imparts some absorption capacity to an absorbent layer, but also may be included to provide a structural matrix to hold dispersed particles of absorbent polymer particles. While inclusion of such particles enhances absorption capacity, keeping such particles suitably dispersed may be important to prevent the particles from "gel-blocking" in use as they swell with absorbed liquid and block the passageways therebetween which allow liquid to move through deposits thereof, compromising absorption capacity. The inclusion of airfelt or other cellulose fiber as a matrix for absorbent polymer particles can serve to reduce or prevent gel-blocking. However, it also imparts bulk to an absorbent layer, even before absorption of any liquids. To reduce the overall size and/or thickness of the absorbent layer, and thereby improve wearer comfort and reduce the bulkiness of the pant for purposes of packaging and shipping volume efficiency, it may be desired to construct a liquid control structure using the lowest volumes of materials possible within performance constraints. Toward this end, examples of suitable materials and constructions for a suitable absorbent structure are described in, but are not limited to, U.S. application Ser. Nos. 12/141,122; 12/141,124; 12/141,126; 12/141,128; 12/141,130; 12/141,132; 12/141,134; 12/141,141; 12/141,143; and 12/141,146; and WO2008/155699. Generally, these applications describe absorbent layer constructions that minimize or eliminate the need for and inclusion of airfelt or other forms of cellulose fiber in combination with particles of absorbent polymer particles. Suitable methods for forming deposits of absorbent polymer particles are additionally disclosed in, for example, EP1621167A2, EP1913914A2 and EP2238953A2. The absorbent polymer particles may be immobilized on the substrate layer. Immobilization may be achieved by applying a thermoplastic adhesive material, which holds and immobilizes the absorbent polymer particles, and cellulose when present, on the substrate layer. Some thermoplastic adhesive material may also penetrate into the layer of absorbent polymer particles and into the substrate layer to provide further immobilization and affixation. The thermoplastic adhesive material may not only help in immobilizing the absorbent polymer particles on the substrate layer but also may help in maintaining the integrity of the channels. The thermoplastic adhesive material avoids that a significant amount of absorbent polymer particles migrates into the channels. Thermoplastic adhesive materials suitable for use in the present disclosure includes hot melt adhesives including at least a thermoplastic polymer in combination with a plasticizer and other thermoplastic diluents such as tackifying resins and additives such as antioxidants. Example suitable hot melt adhesive materials are described in EP1447067A2.

Particularly in diapers for babies older than 12 months, toddlers and young children, it may be important that liquid control structure 15 have absorbent storage capacity sufficient to absorb and effectively retain a substantial quantity of urine. Accordingly, as suggested in FIG. 4, it may be desired that absorbent layer 35 be of a size that causes it to have a substantial volume absorbent capacity. In one example, the absorbent layer 35 may extend over a majority of the plan surface area of the diaper beneath the front topsheet 16 alone, from the attached proximal portion 24 of transverse perineal barrier 23 forward. In another example, the absorbent layer 35 may extend a majority of the length of the diaper 10, and be present not only in the front portion 12 but also in the perineal portion 13 and rear portion 11, and thus be present between the backsheet and the front topsheet, and between the backsheet and the rear topsheet. For purposes of efficient, even and rapid distribution of urine across the entirety of the absorbent layer 35, it may be desired that acquisition layer 34 cover a majority of the plan surface area of the absorbent layer 35.

In some circumstances, it may be desired to use the diaper, additionally or alternatively, as a urine sample collection device. Generally in such circumstances, it may be desired that the diaper be adapted to receive and hold urine discharged by the wearer without substantially retainably absorbing the urine, and without altering the composition of the urine solution, e.g., by contaminating it with soluble materials included as or on components of the diaper in areas in which urine will be received and collected. For example, it may be desired the that the liquid control structure be adapted to provide space for urine to be received and held, but not contain substantial quantities of materials that tend to retainably absorb and/or capture urine constituents. For purposes of maintaining open space between the liquid permeable backsheet and the wearer-facing layer to receive and hold urine, but to prevent it from flowing freely throughout the space, it may be desired that the liquid control structure include a substantially non-absorbent material, for example, a batt of material formed of an accumulation of substantially non-absorbent polymer fibers. To reduce or prevent substantial absorption and/or alteration of the composition of the urine, it may also be desired that the liquid control structure not contain a substantial quantity of water-absorbent material of any of the types typically used in disposable diapers, disposable absorbent pants and other absorbent personal hygiene products, i.e., cellulose/cellulosic fibers; absorbent sponge; absorbent foam; superabsorbent polymer; absorbent gelling material; hydrogel-forming particles; and/or absorbent polymer particles (collectively, "absorbent material"). Thus, it may be desired that at least 50 percent of the volume of the liquid control structure, as defined by its plan surface area, contain no more than 50 percent, more preferably no more than 35 percent, even more preferably no more than 20 percent, or 10 percent, or 5 percent and still more preferably no more than an insubstantial quantity or even about 0 percent, by weight absorbent material. It may be even further preferred that at least 65 percent, or 80 percent, 90 percent, 95 percent or even substantially all of the volume of the liquid control structure, as defined by its plan surface area, contain no more than 50 percent, more preferably no more than 35 percent, even more preferably no more than 20 percent, or 10 percent, or 5 percent and still more preferably no more than an insubstantial quantity or even about 0 percent, by weight absorbent material.

Non-Reliance on Adhesive-to-Skin Contact

As noted, premature and very young infants may have very sensitive and delicate skin. Adhering devices via an adhesive composition may be painfully irritating or even damaging to such an infant's skin. For this reason, it may be deemed desirable in such circumstances that the diaper 10 have no features adapted to be adhered to the wearer's skin and required for use of the diaper.

Exudates Indicator

It may be desired that the diaper 10 include a wetness indicator 40 (see, e.g., FIGS. 3-6) that imparts a visible change of appearance to the diaper on the outside, when urine has entered the space containing the liquid control structure. This can help notify the caregiver that urination has occurred, and promote a prompt removal of the diaper from the patient to, for example, reduce the chance that a stool sample will be contaminated by urine that may escape into the space in the rear portion adapted for receiving the stool sample, or facilitate prompt collection of a urine sample.

The wetness indicator may have any form, composition or configuration suitable for a relatively prompt response. In one example, a wetness indicator may include a material applied or affixed to the wearer-facing surface of the backsheet 14, in the envelope space between the topsheet and the backsheet where urine will be received. In another example, a wetness indicator may include an indicator material applied or affixed to an outward-facing surface of the liquid control structure 35. The indicator material may include a composition selected, formulated and/or adapted to visibly change appearance when wetted, or when warmed by contact with recently discharged urine. The appearance change may be one or more of a change in color, appearance or disappearance of a visible element, or any other visible change that occurs when the composition is wetted or warmed. The material(s) forming urine and feces impermeable backsheet 14 may be selected to have sufficient translucence (e.g., sufficiently low opacity) to enable effectively clear visibility of the wetness indicator on the outside of the diaper, in combination with the materials, composition, configuration and placement location of the wetness indicator 40. Non-limiting suitable examples are described in U.S. provisional applications Ser. Nos. 62/147,258 and 62/186,406. Other non-limiting suitable examples are described in U.S. Pat. Nos. 8,927,801; 8,618,349; 7,332,642; 7,159,532; 6,075,178; and 4,231,370; and U.S. published application nos. 2015/173968; 2013/116644; 2011/137274; and 2004/4254549.

In other examples, an included wetness indicator may operate to electrically/electronically trigger a visible and/or audible signal when the diaper is wetted. In some examples, a combination of a sensing device or devices included in components of the diaper that will be exposed to wetness, and a signal-receiving/processing device, may be included. In such examples, the sensing device in the diaper generates a signal indicative of a wetted condition, and the signal-receiving/processing device receives the signal and provides a visible and/or audible signal to the caregiver. In some examples, the signal-receiving/processing device may be remote from the diaper and may be carried about by the caregiver. Non-limiting examples are described in U.S. Pat. Nos. 9,241,839 and 6,603,403; and U.S. Pat. App. Pub. Nos. 2010/0030173 and 2010/0164733. Various improvements and variations of such examples as well as other configurations of diaper wetness detection devices are described and known in the art.

In still other examples, it may be desired that the diaper include a device adapted to detect, and cause generation of a visible and/or audible signal of, the presence of stool in the diaper. This may provide another means of facilitating the prompt retrieval of an unadulterated stool sample. Non-limiting examples are described in U.S. Pat. No. 8,933,292.

Packaging Configuration and Information

It may be desirable to provide a separate package for each individual diaper. A diaper as described herein may be deemed a product for medical use or treatment. Thus, individual packaging of each diaper may be desirable for purposes of actually or perceivably maintaining a level of sterility, cleanliness, purity and structural integrity of each individual diaper until use, in a manner similar to the manner in which, e.g., individual bandages are packaged. A supply of individually packaged diapers may be packaged as a group in a larger outer package.

In the event that a composition, for example, a water-soluble surfactant, is included in or on materials of the diaper within the space that stool will contact, it may be desirable to include information with the individual or group packaging associated with the diaper, or even on the diaper itself, effective to notify health care and/or analytical personnel of the inclusion of the composition in the diaper. Other information useful for enabling the caregiver to identify, quantify or isolate components or attributes of the stool sample recovered from the diaper may also be included with the packaging. In one additional non-limiting example, the weight of the individual diaper may be recorded on the packaging or on material(s) included with the packaging. This will enable the caregiver to calculate the quantity by weight of stool discharged by the patient, from, e.g., the weight of the diaper prior to use, and the measured weight of the diaper after its removal from the wearer following an elimination event, prior to removal of the sample from the diaper. In one example, such information may be printed on the diaper itself, such as on an outward-facing surface of the backsheet or a visible layer thereof.

It may also be desirable to include information and/or indicia associated with the diaper, individual packaging (if included) or outer packaging, identifying the diaper as a special-use diaper, and distinguishing it from ordinary diapers. This will serve to notify healthcare professionals or other caregivers of the special design of the diaper, and help avoid confusion, inappropriate use of the special-use diaper for ordinary purposes, and intermixing of supplies of the special-use diapers with supplies of ordinary diapers.

Non-Invasive Method for Collecting Stool Sample from an Infant

Utilizing a suitable example of a diaper 10 as described herein, a health care professional or caregiver may obtain a stool sample from an infant by the following steps:

Applying the diaper to a patient-wearer in the same manner as a conventional disposable diaper;

Detecting an event of elimination by the patient-wearer; this may include observing the wearer for facial, audible or body-language signals that he or she has eliminated; feeling the diaper to detect the presence of stool; or observing a change in appearance of the diaper resulting from the presence of stool;

Removing the diaper from the patient-wearer;

Locating the diaper proximate to a sample container; and

Emptying the stool from the diaper into the sample container.

The above-described method, employing an example of a diaper as described herein, may provide improved facilitation in obtaining a stool sample from an infant, without the need for invasive devices or techniques or the application of an adhesive to the infant's skin.

Opacity Test Method

The opacity of a backsheet material is the degree to which light is blocked by that material. A higher opacity value indicates a higher degree of light block by the material. Opacity may be measured using a 0° illumination/45° detection, circumferential optical geometry, spectrophotometer with a computer interface such as the HunterLab Lab Scan XE running Universal Software (available from Hunter Associates Laboratory Inc., Reston, Va.). Instrument calibration and measurements are made using the standard white and black calibration plates provided by the vendor. All testing is performed in a room maintained at about 23±2° C. and about 50±2% relative humidity.

Configure the spectrophotometer for the XYZ color scale, D65 illuminant, 10° standard observer, with UV filter set to nominal. Standardize the instrument according to the manufacturer's procedures using the 1.20 inch port size and 1.00 inch area view. After calibration, set the software to the Y opacity procedure.

To obtain the specimen, lay the diaper sample flat on a bench, body facing surface downward, and measure the total longitudinal length of the diaper. Note a site 33% of the total length from the rear waist edge of the diaper along the longitudinal axis. Carefully remove the backsheet including any and all laminate components thereof, from the outward-facing side of the diaper. A cryogenic spray, such as Cyto-Freeze (obtained from Control Company, Houston, Tex.), may be used to separate the backsheet laminate from the other components of the diaper. Cut a piece 50.8 mm by 50.8 mm centered at the site identified above. Precondition specimens at about 23° C.±2° C. and about 50%±2% relative humidity for 2 hours prior to testing.

Place the specimen over the measurement port. The specimen should completely cover the port with the surface corresponding to the garment-facing surface of the diaper directed toward the port. Cover the specimen with the white standard plate. Take a reading, then remove the white tile and replace it with black standard tile without moving the specimen. Obtain a second reading, and calculate the opacity as follows:

$$\text{Opacity} = Y\text{value(black backing)}/Y\text{value(white backing)} \times 100 \qquad 5$$

A total of 10 identical diapers are analyzed and their opacity results recorded. Calculate and report the average opacity and standard deviation for the 10 backsheet laminate measurements to the nearest 0.01%.

In view of the foregoing description, the following examples are contemplated:

1. A disposable diaper having a length and a front portion, a rear portion and a perineal portion between the front and rear portions, and comprising:
   a backsheet comprising an effectively urine and feces impermeable material;
   a transverse perineal barrier in the perineal portion comprising an effectively urine and feces impermeable material and having a proximal portion directly or indirectly overlying the backsheet and sealingly connected to any other component of the diaper, and a free distal edge;
   a liquid control structure disposed over the backsheet and forward of the transverse perineal barrier.
2. The diaper of example 1 further comprising a front upper layer comprising an effectively urine permeable material, overlying the liquid control structure in the front portion.
3. The diaper of either of the preceding examples further comprising left and right standing longitudinal cuffs each extending from the front portion to the rear portion and having a proximal cuff portion, and a free longitudinal cuff distal edge, each longitudinal cuff comprising a longitudinal cuff elastic member proximate the free longitudinal cuff distal edge, the longitudinal cuff elastic member being incorporated into the longitudinal cuff in a pre-strained condition so as to cause material forming the free longitudinal cuff distal edge to gather and extend toward a wearer's skin when the diaper is worn.
4. The diaper of example 3 wherein the longitudinal cuffs comprise effectively urine and feces impermeable material.
5. The diaper of either of examples 3 or 4 wherein the longitudinal cuffs comprise polymeric film.
6. The diaper of any of examples 3-5 wherein the transverse perineal barrier has left and right side edges each respectively attached to a left or right longitudinal cuff.
7. A disposable diaper having a length and a front portion, a rear portion and a perineal portion between the front and rear portions, and comprising:
   a backsheet comprising an effectively urine and feces impermeable material;
   a liquid control structure disposed over the backsheet and extending from the front portion to the rear portion;
   a rear upper layer comprising an effectively feces impermeable material, overlying the liquid control structure in the rear portion; and
   a transverse perineal barrier in the perineal portion comprising an effectively urine and feces impermeable material and having a proximal portion directly or indirectly overlying the backsheet and directly or indirectly sealingly connected to any other component of the diaper, and a free distal edge.
8. The diaper of example 7 wherein the rear upper layer comprises polymeric film.
9. The diaper of either of examples 7 or 8 further comprising a front upper layer comprising an effectively urine permeable material, overlying the liquid control structure in the front portion.
10. The diaper of example 9 wherein the front upper layer and the rear upper layer are formed at least in part of a common section of material.
11. The diaper of any of examples 7-10 wherein the rear upper layer and the transverse perineal barrier are formed at least in part of a common section of material.
12. The diaper of any of examples 7-11 further comprising left and right standing longitudinal cuffs each extending from the front portion to the rear portion and having a proximal cuff portion, and a free longitudinal cuff distal edge, each longitudinal cuff comprising a longitudinal cuff elastic member proximate the free longitudinal cuff distal edge, the longitudinal cuff elastic member being incorporated into the longitudinal cuff in a pre-strained condition so as to cause material forming the free longitudinal cuff distal edge to gather and extend toward a wearer's skin when the diaper is worn.
13. The diaper of example 12 wherein the longitudinal cuffs comprise effectively urine and feces impermeable material.
14. The diaper of either of examples 12 or 13 wherein the longitudinal cuffs comprise polymeric film.
15. The diaper of any of examples 12-14 wherein the transverse perineal barrier has left and right side edges each respectively attached to a left or right longitudinal cuff
16. The diaper any of examples 12-15, wherein the rear upper layer and the longitudinal cuffs are formed at least in part of a common section of material.
17. The diaper of any of the preceding examples wherein the transverse perineal barrier comprises a perineal barrier elastic member proximate the free distal edge.
18. The diaper of any of the preceding examples comprising a transverse rear cuff disposed in the rear portion, having an attached rear cuff portion attached to any other component of the diaper and a free transverse rear cuff distal edge.
19. The diaper of example 18 wherein the transverse rear cuff comprises a rear cuff elastic member proximate the free transverse rear cuff distal edge.
20. The diaper of either of examples 18 or 19 wherein the rear cuff comprises effectively feces impermeable material.
21. A disposable diaper having a length and a front portion, a rear portion and a perineal portion between the front and rear portions, and comprising:
   a backsheet comprising an effectively urine and feces impermeable material;
   a liquid control structure overlying the backsheet; and
   an upper layer overlying the liquid control structure, comprising an effectively feces impermeable zone.
22. The diaper of example 21 wherein the effectively feces impermeable zone is present in the rear portion.
23. The diaper of either of examples 21 or 22 wherein the effectively feces impermeable zone comprises a polymeric film.
24. The diaper of any of examples 21-23 further comprising left and right standing longitudinal cuffs each extending from the front portion to the rear portion and having a proximal cuff portion, and a free longitudinal cuff distal edge, each longitudinal cuff comprising a longitudinal cuff elastic member proximate the free longitudinal cuff distal edge, the longitudinal cuff elastic member being incorporated into the longitudinal cuff in a pre-strained condition so as to cause material forming the free longitudinal cuff distal edge to gather and extend toward a wearer's skin when the diaper is worn.

25. The diaper of example 24 wherein the longitudinal cuffs comprise an effectively urine and feces impermeable material.

26. The diaper of either of examples 24 or 25 wherein the longitudinal cuffs comprise a polymer film.

27. The diaper of any of examples 24-26 wherein the longitudinal cuffs and the layer are formed at least in part of a common section of material.

28. The diaper of any of examples 21-27 wherein the liquid control structure has a first width and the feces impermeable zone has a second width greater than the first width.

29. The diaper of any of examples 24-28 wherein the urine and feces impermeable zone overlaps the proximal cuff portion of each longitudinal cuff.

30. The diaper of any of examples 21-29 further comprising a transverse perineal barrier in the perineal portion comprising an effectively urine and feces impermeable material and having a proximal portion directly or indirectly overlying the backsheet and directly or indirectly sealingly connected to any other component of the diaper, and a free perineal barrier distal edge.

31. The diaper of example 30 wherein the transverse perineal barrier comprises a perineal barrier elastic member proximate the free perineal barrier distal edge.

32. The diaper of either of examples 30 or 31 wherein the perineal barrier and the feces impermeable zone of the layer are formed at least in part of a common section of material.

33. The diaper of any of examples 21-32 wherein the feces impermeable zone overlies the liquid control structure.

34. The diaper of any of examples 21-33 further comprising a transverse rear cuff disposed in the rear portion, having an attached rear cuff portion directly or indirectly overlying the backsheet and attached to any other component of the diaper, and a free transverse rear cuff distal edge.

35. The diaper of example 34 wherein the transverse rear cuff comprises a rear cuff elastic member proximate the rear cuff distal edge.

36. The diaper of either of examples 34 or 35 wherein the rear cuff comprises an effectively feces impermeable material.

37. The diaper of any of examples 34-36 wherein the transverse rear cuff and the feces impermeable zone of the layer are formed at least in part of a common section of material.

38. The diaper of any of examples 21-37 wherein the upper layer or a second upper layer comprises an effectively urine permeable zone.

39. The diaper of example 38 wherein the effectively urine permeable zone is disposed at least in the front portion of the diaper.

40. The diaper of any of the preceding examples further comprising a component of an exudates indicator.

41. The diaper of any of examples 3, 12, 24 or any examples dependent on examples 3, 12 or 24 wherein the proximal cuff portion is connected to an underlying component of the diaper.

42. The diaper of example 41 wherein the proximal cuff portion is indirectly or directly sealingly connected to the underlying component.

43. The diaper of any of examples 3, 12, 24 or any examples dependent on examples 3, 12 or 24 further comprising left and right second standing longitudinal cuffs.

44. The diaper of any of examples 1-20 or examples 30-32 wherein the transverse perineal barrier comprises a marginal portion proximate to the free distal edge thereof, configured to lay flat against a wearer's skin when the diaper is worn.

45. The diaper of any of the preceding examples wherein the liquid control structure has a plan surface area in an x-y plane and a volume coextensive with the plan surface area, and a portion of the volume defined by at least 50 percent of the plan surface area contains no more than 50 percent by weight absorbent material.

46. The diaper of any of the preceding examples, packaged in an individual package.

47. A package containing a plurality of individually packaged diapers of example 46.

48. The diaper of any of the preceding examples, bearing, associated with or accompanied by information and/or one or more indicia effectively identifying the diaper as a special use diaper.

49. A method of obtaining a stool sample from an infant, comprising the steps of:
applying a diaper to the infant;
detecting an event of elimination by the infant;
removing the diaper from the infant;
locating the diaper proximate to a sample container; and
emptying stool from the diaper into the sample container.

50. The method of example 49 wherein the diaper is the diaper of any of examples 1-46 or 48.

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper comprising a length, a front portion, a front end edge, a rear portion, a rear end edge, and a perineal portion between the front portion and the rear portion, the disposable diaper further comprising:
a backsheet that is urine impermeable and feces impermeable;

a first topsheet that is urine permeable, wherein the first topsheet directly or indirectly overlies at least part of the backsheet, and wherein the first topsheet is disposed in at least the front portion of the disposable diaper;

a second topsheet that is urine impermeable and feces impermeable, wherein the second topsheet directly or indirectly overlies at least part of the backsheet, and wherein the second topsheet is disposed only in the perineal portion and the rear portion of the disposable diaper;

a left standing longitudinal cuff and a right standing longitudinal cuff, where each of the left standing longitudinal cuff and the right standing longitudinal cuff are urine impermeable and feces impermeable, and extend from the front portion to the rear portion;

a transverse perineal barrier that is urine impermeable and feces impermeable, and comprises a first proximal edge, a first left edge, a first right edge, and a first distal edge, wherein the transverse perineal barrier is disposed in the perineal portion of the disposable diaper, wherein the transverse perineal barrier is attached to at least one of the second topsheet or the first topsheet, and wherein the first left edge is attached to the left standing longitudinal cuff, and the first right edge is attached to the right standing longitudinal cuff;

a liquid control structure disposed over at least part of the backsheet and between the front end edge and the transverse perineal barrier; and a transverse rear cuff that is urine impermeable and feces impermeable, and comprises a second proximal edge, a second left edge, a second right edge, and a second distal edge, wherein the transverse rear cuff is disposed in the rear portion of the disposable diaper, wherein the second proximal edge is attached to the second topsheet, and wherein the second left edge is attached to the left standing longitudinal cuff, and the second right edge is attached to the right standing longitudinal cuff.

2. The disposable diaper of claim 1, wherein each of the left standing longitudinal cuff and the right standing longitudinal cuff comprise a proximal cuff portion, a free longitudinal cuff distal edge, and a longitudinal cuff elastic member proximate the free longitudinal cuff distal edge, the longitudinal cuff elastic member being in a pre-strained condition so as to cause material forming the free longitudinal cuff distal edge to gather and extend toward a wearer's skin when the disposable diaper is worn.

3. The disposable diaper of claim 1, wherein the first distal edge and the second distal edge are free of attachment to any other component of the disposable diaper.

4. The disposable diaper of claim 1, wherein the left standing longitudinal cuff and the right standing longitudinal cuff comprise a polymeric film.

5. The disposable diaper of claim 2, further comprising an exudates indicator.

6. A disposable diaper comprising a length, a front portion, a rear portion, and a perineal portion between the front portion and the rear portion, further comprising:

a backsheet that is urine impermeable and feces impermeable;

a liquid control structure overlying at least part of the backsheet and extending from the front portion to the rear portion;

a first topsheet that is urine permeable, wherein the first topsheet directly or indirectly overlies the liquid control structure, and wherein the first topsheet extends across the front portion, the rear portion, and the perineal portion of the disposable diaper;

a second topsheet that is urine impermeable and feces impermeable, wherein the second topsheet is a discrete element discontinuous with the first topsheet, and wherein the second topsheet directly or indirectly overlies at least part of the first topsheet in the rear portion; and a left standing longitudinal cuff and a right standing longitudinal cuff, where each of the left standing longitudinal cuff and the right standing longitudinal cuff are urine impermeable and feces impermeable, and extend from the front portion to the rear portion;

a transverse perineal barrier that is urine impermeable and feces impermeable, and comprises a first proximal edge, a first left edge, a first right edge, and a first distal edge, wherein the transverse perineal barrier is disposed in the perineal portion of the disposable diaper, wherein the transverse perineal barrier is attached to at least one of the second topsheet or the first topsheet, and wherein the first left edge is attached to the left standing longitudinal cuff, and the first right edge is attached to the right standing longitudinal cuff; and a transverse rear cuff that is urine impermeable and feces impermeable, and comprises a second proximal edge, a second left edge, a second right edge, and a second distal edge, wherein the transverse rear cuff is disposed in the rear portion of the disposable diaper, wherein the second proximal edge is attached to the second topsheet, and wherein the second left edge is attached to the left standing longitudinal cuff, and the second right edge is attached to the right standing longitudinal cuff.

7. The disposable diaper of claim 6, wherein the second topsheet comprises a polymeric film.

8. The disposable diaper of claim 6, wherein each of the left standing longitudinal cuff and the right standing longitudinal cuff comprise a proximal cuff portion, a free longitudinal cuff distal edge, and a longitudinal cuff elastic member proximate the free longitudinal cuff distal edge, the longitudinal cuff elastic member being in a pre-strained condition so as to cause material forming the free longitudinal cuff distal edge to gather and extend toward a wearer's skin when the disposable diaper is worn.

9. The disposable diaper of claim 6, wherein the first distal edge and the second distal edge are free of attachment to any other component of the disposable diaper.

10. The disposable diaper of claim 8, wherein the left standing longitudinal cuff and the right standing longitudinal cuff comprise a polymeric film.

11. The disposable diaper of claim 6, further comprising an exudates indicator.

12. The disposable diaper of claim 1, wherein the transverse perineal barrier comprises a perineal barrier elastic member proximate the first distal edge.

13. The disposable diaper of claim 1, further comprising a wetness indicator.

14. The disposable diaper of claim 1, wherein the transverse rear cuff comprises a rear cuff elastic member proximate the second distal edge.

15. A method of obtaining a stool sample from an infant, comprising the steps of:

applying the disposable diaper of claim 6 to the infant;
detecting an event of elimination by the infant;
removing the disposable diaper from the infant;
locating the disposable diaper proximate to a sample container; and
emptying stool from the disposable diaper into the sample container.

16. The disposable diaper of claim 1, wherein the second topsheet comprises a polymeric film.

17. The disposable diaper of claim 12, wherein the perineal barrier elastic member comprises a flattened strip of elastomeric material.

* * * * *